US012605478B2

(12) United States Patent
Prasad et al.

(10) Patent No.: US 12,605,478 B2
(45) Date of Patent: Apr. 21, 2026

(54) DISINFECTION DEVICE WITH FATIGUE-BASED INDICATOR

(71) Applicant: Becton, Dickinson and Company, Franklin Lakes, NJ (US)

(72) Inventors: Shishir Prasad, Ramsey, NJ (US); Mohammed Mehtab Khan, Bangalore (IN); Prasad Govindaraj, Coimbatore (IN); Kaushik Suman, Jharkhand (IN); Aniket Kulkarni, Pune (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 672 days.

(21) Appl. No.: 18/093,625

(22) Filed: Jan. 5, 2023

(65) Prior Publication Data

US 2024/0226356 A1     Jul. 11, 2024

(51) Int. Cl.
| | |
|---|---|
| *A61L 2/18* | (2026.01) |
| *A61L 2/26* | (2006.01) |
| *A61L 101/34* | (2006.01) |
| *A61L 103/15* | (2026.01) |

(52) U.S. Cl.
CPC ..... *A61L 2/18* (2013.01); *A61L 2/26* (2013.01); *A61L 2101/34* (2020.08); *A61L 2103/15* (2026.01); *A61L 2202/121* (2013.01); *A61L 2202/122* (2013.01); *A61L 2202/123* (2013.01)

(58) Field of Classification Search
CPC .. A61M 39/16; A61M 39/162; A61M 39/165; A61M 2205/0205; A61L 2/18; A61L 2/26; A61L 2101/34; A61L 2202/24; A61L 2202/121; A61L 2202/122; A61L 2202/123
See application file for complete search history.

(56) References Cited

U.S. PATENT DOCUMENTS

| | | | |
|---|---|---|---|
| 10,744,316 B2 | 8/2020 | Fangrow | |
| 2008/0021392 A1* | 1/2008 | Lurvey | A61M 39/16 604/111 |
| 2010/0047123 A1 | 2/2010 | Solomon et al. | |
| 2014/0366914 A1* | 12/2014 | Kerr | A61B 1/122 15/104.93 |
| 2018/0055962 A1 | 3/2018 | Drmanovic | |
| 2019/0151502 A1 | 5/2019 | Brosig et al. | |
| 2019/0209781 A1 | 7/2019 | Solomon et al. | |
| 2020/0276346 A1 | 9/2020 | Drmanovic | |
| 2020/0330741 A1 | 10/2020 | Fangrow | |
| 2021/0138223 A1 | 5/2021 | Jiang et al. | |
| 2021/0146113 A1 | 5/2021 | Browka et al. | |
| 2021/0170157 A1 | 6/2021 | Grant et al. | |
| 2021/0316130 A1 | 10/2021 | Anderson et al. | |
| 2021/0322749 A1 | 10/2021 | Rothenberg et al. | |
| 2023/0355950 A1* | 11/2023 | Leone | A61M 39/162 |

* cited by examiner

*Primary Examiner* — Jennifer Wecker
*Assistant Examiner* — Brady C Pilsbury
(74) *Attorney, Agent, or Firm* — Servilla Whitney LLC

(57) ABSTRACT

Provided herein is a disinfecting device, including a housing having a proximal end, a distal end having an opening therein, and a sidewall therebetween defining an interior in fluid communication with the opening, one or more flanges arranged at the distal end of the housing, and a disinfecting solution received within the interior, wherein the sidewall includes a deformable portion adjacent the distal end.

21 Claims, 9 Drawing Sheets

DISINFECTION DEVICE WITH FATIGUE-BASED INDICATOR

BACKGROUND OF THE INVENTION

Field of the Invention

The present disclosure relates generally to devices, systems, and kits for disinfecting medical devices.

Description of Related Art

Contamination through a catheter hub of an indwelling catheter assembly is a major source for catheter-related bloodstream infection, especially catheters that remain indwelling for more than 10 days. INS's 2021 Infusion Therapy Standards of Practice recommends disinfecting needle-free connectors (NFCs) before each entry or access. These guidelines also provide recommendations on how to disinfect the NFC, along with recommendations for manufacturers of NFC-disinfection scrubbing devices. However, the disinfection process and duration remain highly variable, and insufficient scrubbing of an NFC could lead to bloodstream infection.

Currently available NFC-disinfecting devices, either scrubbing devices or disinfecting pads, do not offer visual indicia of the disinfection process completion. Incomplete disinfection process has the risk of hub and catheter contamination, which may result in catheter-related bloodstream infection. Accordingly, there is a need in the art for improved devices for disinfecting NFCs.

SUMMARY OF THE INVENTION

Provided herein is a disinfecting device, including a housing having a proximal end, a distal end having an opening therein, and a sidewall therebetween defining an interior in fluid communication with the opening, one or more flanges arranged at the distal end of the housing, and a disinfecting solution received within the interior, wherein the sidewall includes a deformable portion adjacent the distal end.

Provided herein is a disinfecting device as described above and further including a porous material received within the interior.

Provided herein is a disinfecting device as described above wherein the disinfecting solution is received within the porous material.

Provided herein is a disinfecting device as described above, wherein the deformable portion comprises a web comprising one or more openings in the sidewall.

Provided herein is a disinfecting device as described above, wherein the one or more flanges are configured to snap-fit to a medical connector, optionally a needle-free connector (NFC).

Provided herein is a disinfecting device as described above, wherein the one or more flanges are configured such that the disinfecting device is rotatable relative to the medical connector.

Provided herein is a disinfecting device as described above, further including a longitudinally extending section within the interior.

Provided herein is a disinfecting device as described above, further including a removable film arranged over the distal end of the housing.

Provided herein is a disinfecting device as described above, wherein the disinfecting solution comprises chlorhexidine gluconate (CHG).

Provided herein is a disinfecting device as described above, wherein the disinfecting solution comprises isopropyl alcohol (IPA).

Provided herein is a disinfecting device as described above, wherein the disinfecting solution comprises from about 0.5% to about 4% CHG and about 70% IPA.

Provided herein is a disinfecting device as described above, wherein the disinfecting solution comprises about 2% CHG and about 70% IPA.

Provided herein is a disinfecting device as described above, wherein the deformable portion comprises a mechanophoric material.

Provided herein is a disinfecting device as described above, wherein the mechanophoric material is a mechanochromic material.

Provided herein is a disinfecting device as described above, wherein the deformable portion is frangible Also provided herein is a system including a medical connector having a proximal end, a distal end, and a sidewall therebetween defining a fluid conduit and a disinfecting device, the disinfecting device including a housing having a proximal end, a distal end having an opening therein, and a sidewall therebetween defining an interior in fluid communication with the opening, one or more flanges arranged at the distal end of the housing, and a disinfecting solution received within the interior, wherein the sidewall includes a deformable portion adjacent the distal end coupled to the proximal end of the medical connector.

Provided herein is a system as described above, wherein the medical connector is a needle-free connector (NFC)

Provided herein is a system as described above, wherein the connector comprises a threaded proximal end.

Provided herein is a system as described above, wherein the one or more flanges are configured to snap-fit to the medical connector.

Provided herein is a system as described above, wherein the one or more flanges are configured such that the disinfecting device is rotatable relative to the medical connector.

Also provided herein is a kit including a disinfecting device, the disinfecting device including a housing having a proximal end, a distal end having an opening therein, and a sidewall therebetween defining an interior in fluid communication with the opening, one or more flanges arranged at the distal end of the housing, and a disinfecting solution received within the interior, wherein the sidewall includes a deformable portion adjacent the distal end and a packaging defining an interior in which the disinfecting device is received

DESCRIPTION OF THE INVENTION

Figure 1B:
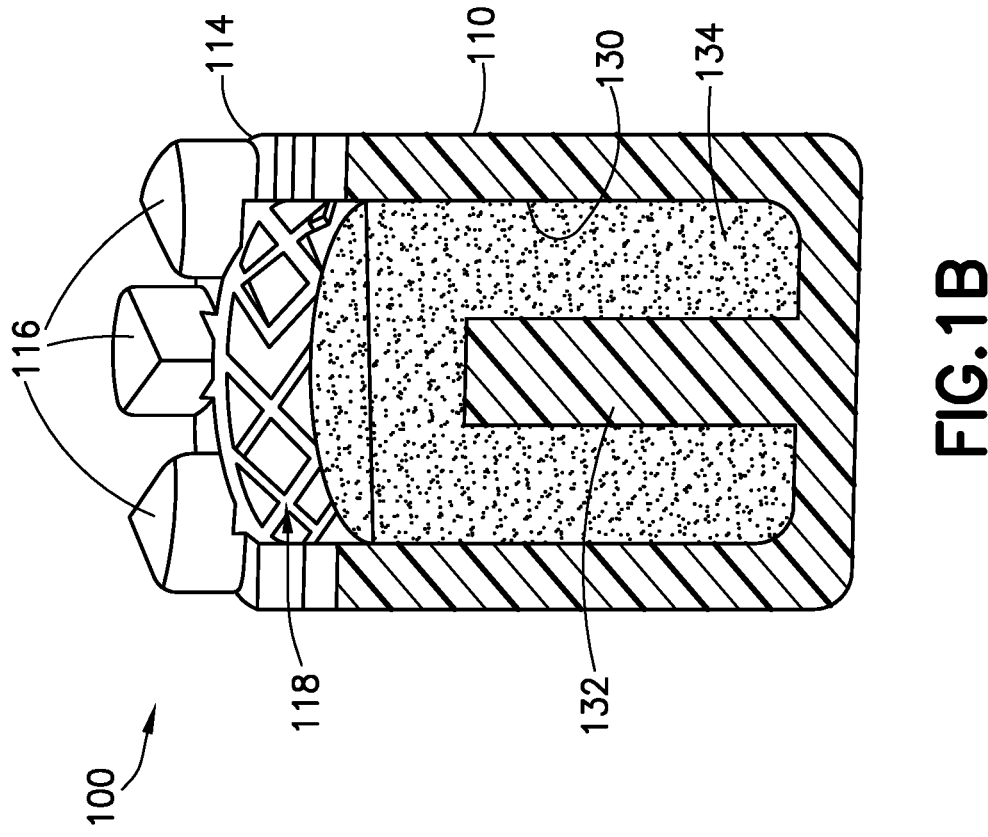
FIG. 1B is a cross-sectional view of a disinfection device according to non-limiting embodiments described herein.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

It should be understood that any numerical range recited herein is intended to include all values and sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

Provided herein are devices, systems, and kits for providing improved disinfection of medical devices, such as medical connectors. Such devices, and the systems and kits in which they are included, provide straightforward indications of prior use and adequate disinfection of medical devices, thus increasing safety and minimizing the risk of contamination.

Figure 1A:
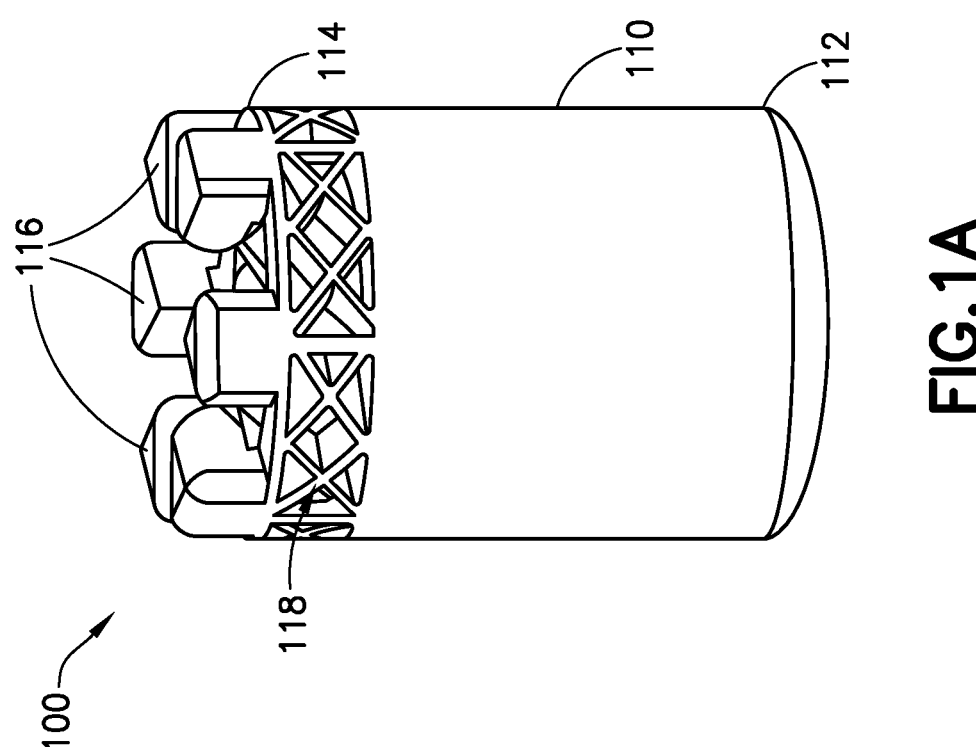
FIG. 1A is a side view of a disinfection device according to non-limiting embodiments described herein.

Turning to FIGS. 1A and 1B, shown is a non-limiting embodiment of a disinfecting device 100 including a housing 110 having a proximal end 112, an open distal end 114, and a sidewall therebetween defining an interior 130. The interior 130 may be configured to receive a disinfection solution therein, optionally received and/or absorbed within a porous material 134 arranged within interior 130. Porous material 134 may be a sponge or other suitable material that can receive a disinfecting solution and/or provide an abrasive surface for disinfecting a medical device to which the disinfecting device 100 is coupled. In non-limiting embodiments, such as shown in FIG. 1B, interior 130 of housing

110 may include a projection 132, which may be arranged to provide mechanical support to at least a portion of porous material 134 received within interior 130 to, for example, aid in improving contact between porous material 134 holding a disinfection solution and a medical device to which housing 110 is coupled. Housing 110 may be formed of any suitable material, such as plastics, thermoplastic and/or thermoset polymers, polypropylene, polyethylene, thermoplastic rubber, and/or thermoset rubber, and may be opaque, at least partially opaque, at least partially translucent, translucent, at least partially transparent, and/or transparent, and may assume any useful shape and configuration, including an elongated cylindrical shape as shown in the accompanying figures. In non-limiting embodiments, a removable film, such as a peelable film, is arranged on distal end 114 of housing 110, providing liquid-tight and/or air-tight protection of distal end 114, porous material 134, and/or a disinfection solution received within interior 130.

Figures 4A, 4B:
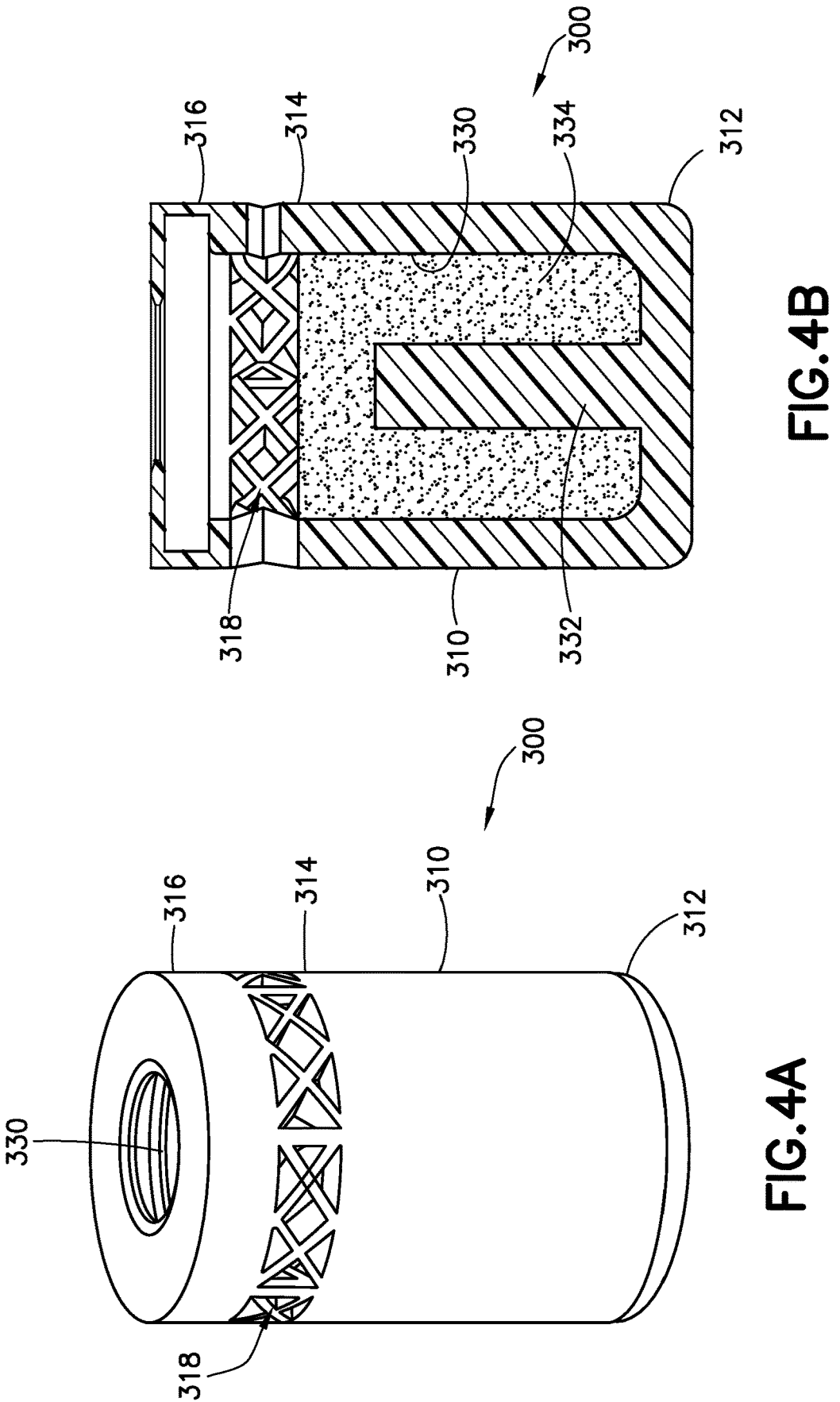
FIG. 4A is a side view of a disinfection device according to non-limiting embodiments described herein.
FIG. 4B is a cross-sectional view of a disinfection device according to non-limiting embodiments described herein.

Housing 110 may include at distal end 114 thereof one or more flanges 116. A non-limiting embodiment of an arrangement of a plurality of flanges 116 is shown in FIGS. 1A and 1B, but those of skill in the art will appreciate that any number and orientation of flanges may be utilized, so long as distal end 114 of housing 110 may be coupled to a medical device. In non-limiting embodiments, one or more flanges 116 enable a snap-fit between housing 110 and a medical device, such as a medical connector. In non-limiting embodiments, one or more flanges 116 define a central opening into which a medical device can be inserted, for example to snap-fit the medical device to housing 110. In non-limiting embodiments, for example as shown in FIGS. 1A and 1B, one or more flanges 116 may assume an "L" shape, with a radially inward-extending portion that allows for a snap-fit to a medical device, such as a medical connector. In other non-limiting embodiments, for example as shown in FIGS. 4A and 4B, flange 316 is a single flange that extends about the circumference of the housing 310, defining a central opening into which a medical device can be inserted, for example to snap-fit the medical device to housing 310.

With continuing reference to FIGS. 1A and 1B, in non-limiting embodiments housing 110 includes a deformable portion 118. Deformable portion 118 may be a thinning of sidewall of housing 110, may be a web with one or more openings in sidewall of housing 110 (e.g., as shown in the attached figures), may include a different (e.g., weaker) material than the remainder of housing 110, and/or or any other known construction for providing one or more weaker points that are deformable. In non-limiting embodiments, deformable portion 118 is frangible, such that a distal end 114 of housing 110, for example including one or more flanges 116, is separable from the remainder of housing 110 upon the breaking of the deformable portion 118. In non-limiting embodiments, deformable portion 118 includes a mechanophoric material. As used herein, "mechanophoric" means a material that undergoes a reaction triggered by a mechanical force. Mechanophoric materials are known to those of skill in the art, for example as set forth in the article by Chen et al., "Mechanochemical tools for polymer materials." (*Chem Soc. Rev.* 2021, 50: 4100-4140), the content of which is incorporated herein by reference in its entirety. In non-limiting embodiments, the deformable portion includes a mechanochromic material. As used herein, "mechanochromic" means a material that changes its absorption spectrum upon application of a mechanical force. As used herein, "mechanochromic" also includes mechanofluorescent and mechanoluminescent materials.

Suitable disinfecting solutions for medical devices, such as medical connectors, are known to those of skill in the art, and may include, for example, chlorhexidine gluconate (CHG) and alcohols, such as isopropyl alcohol (IPA). In non-limiting embodiments, the disinfecting solution includes about 0.5% to about 4% CHG, optionally, about 2% CHG, and/or about 70% IPA. In non-limiting embodiments, the disinfecting solution includes about 2% CHG and about 70% IPA.

Housing 110 may have one or more labels arranged thereon, for example identifying the contents held therein.

Figure 2A:
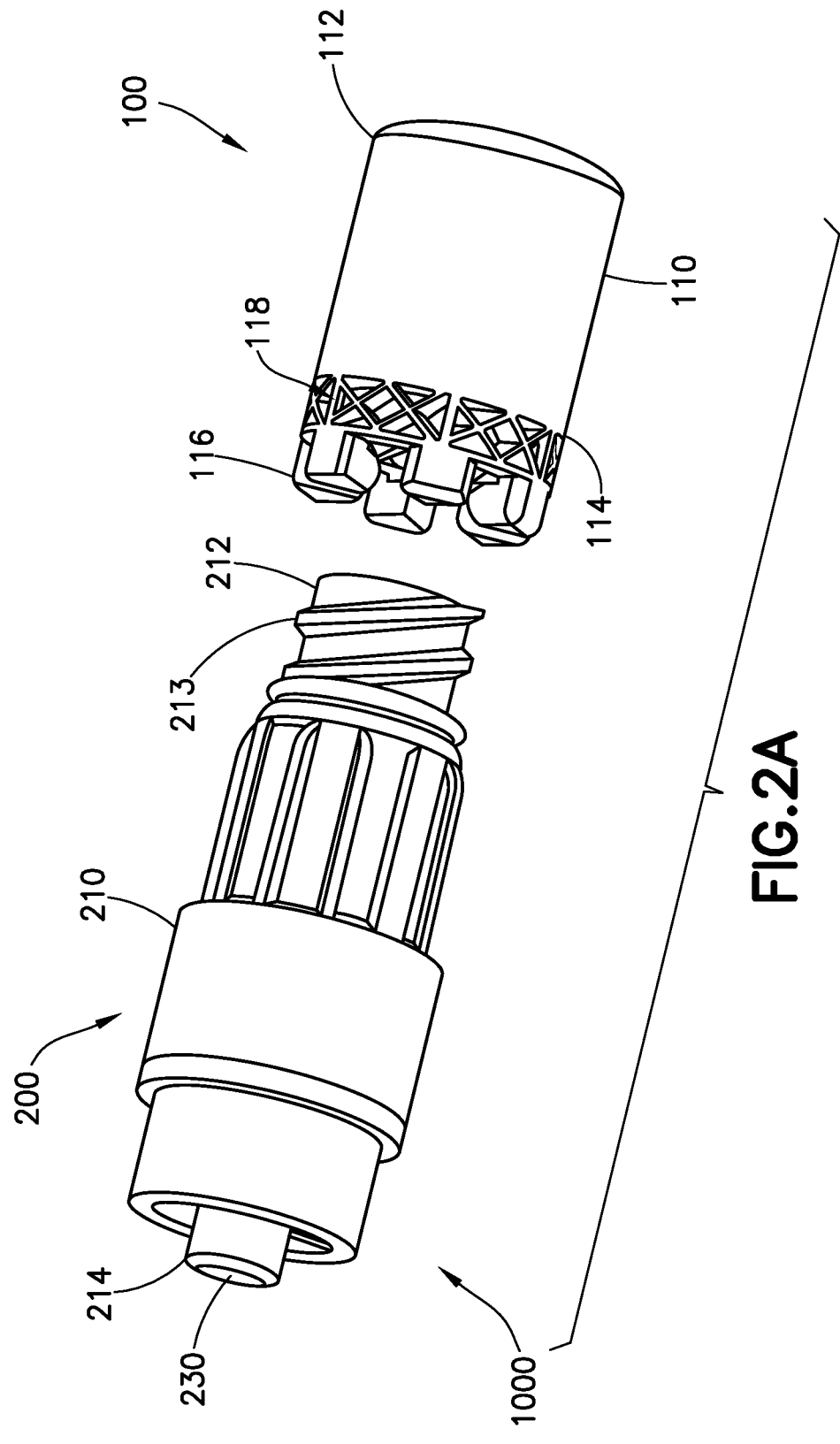
FIG. 2A is an exploded view of a system including a disinfection device according to non-limiting embodiments described herein.
Figure 2B:
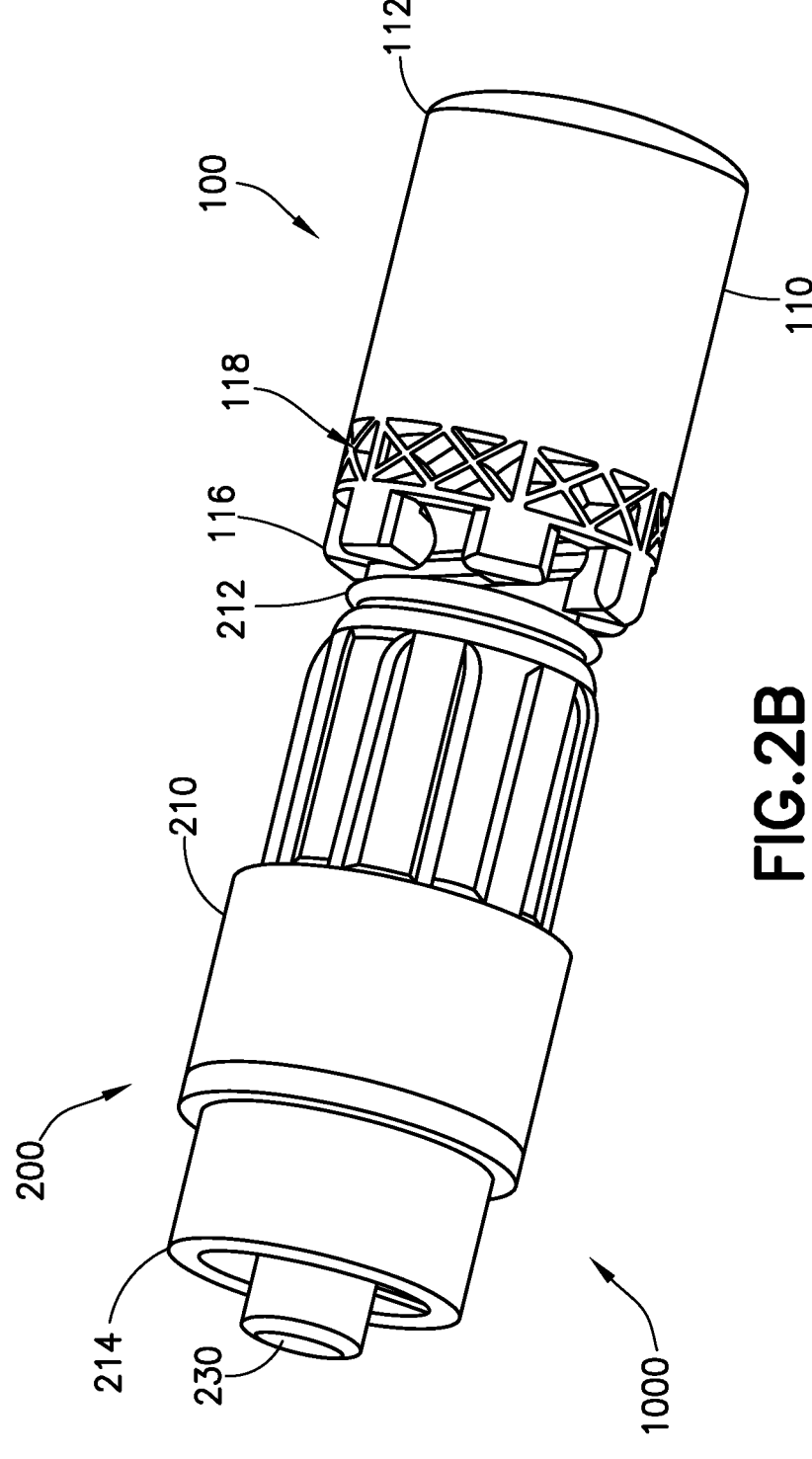
FIG. 2B is a perspective view of a system including a disinfection device according to non-limiting embodiments described herein.
Figure 2C:
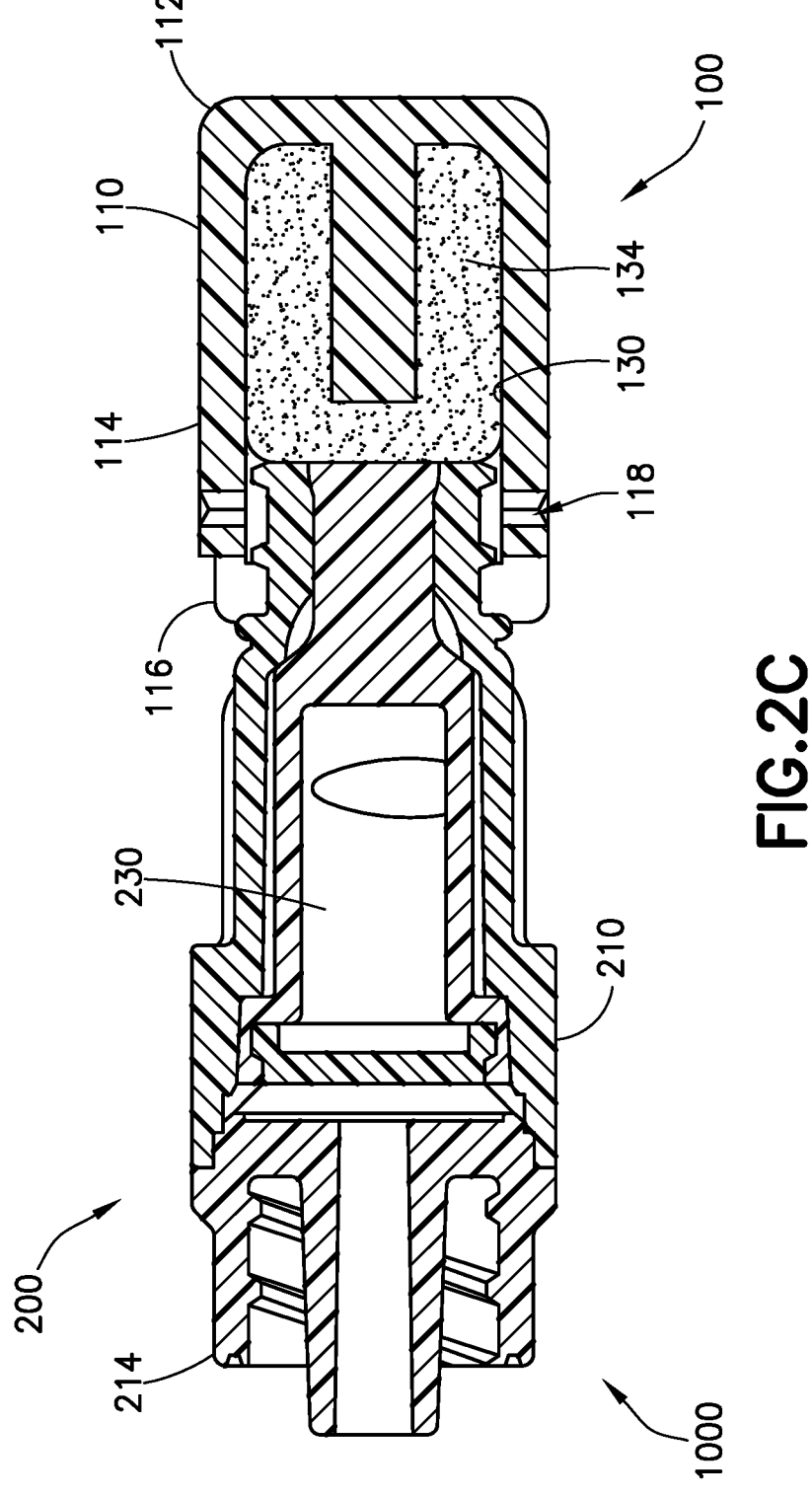
FIG. 2C is a cross-sectional view of a system including a disinfection device according to non-limiting embodiments described herein.

Turning to FIGS. 2A-2C, shown are non-limiting embodiments of a disinfecting device 100, useful in a system 1000 with a medical device 200. Disinfecting device 100 may be as substantially described herein. Medical device 200 may be any suitable medical device, and in the illustrated embodiments is a medical connector, such as a needle-free connector (NFC). Medical device 200 may include a housing 210 having a proximal end 212 and a distal end 214 and a sidewall defining a fluid conduit 230. Proximal end 212 of device 200 may include any features for allowing connection with disinfecting device 100 or other medical devices, such as flange(s), thread(s), and/or the like. As shown in FIGS. 2B and 2C, disinfection device 100 may be coupled to proximal end 212 of medical device 200 by one or more flanges 116. In this position, proximal end of medical device 200 may be in contact with porous material 134 received within interior 130 of disinfection device 100. Disinfection device 100 may be rotatable relative to medical device 200, allowing for scrubbing of proximal end 212 of medical device 200 by porous material 134 and for disinfecting by a disinfection solution received within interior 130 of disinfecting device 100.

Figure 3:
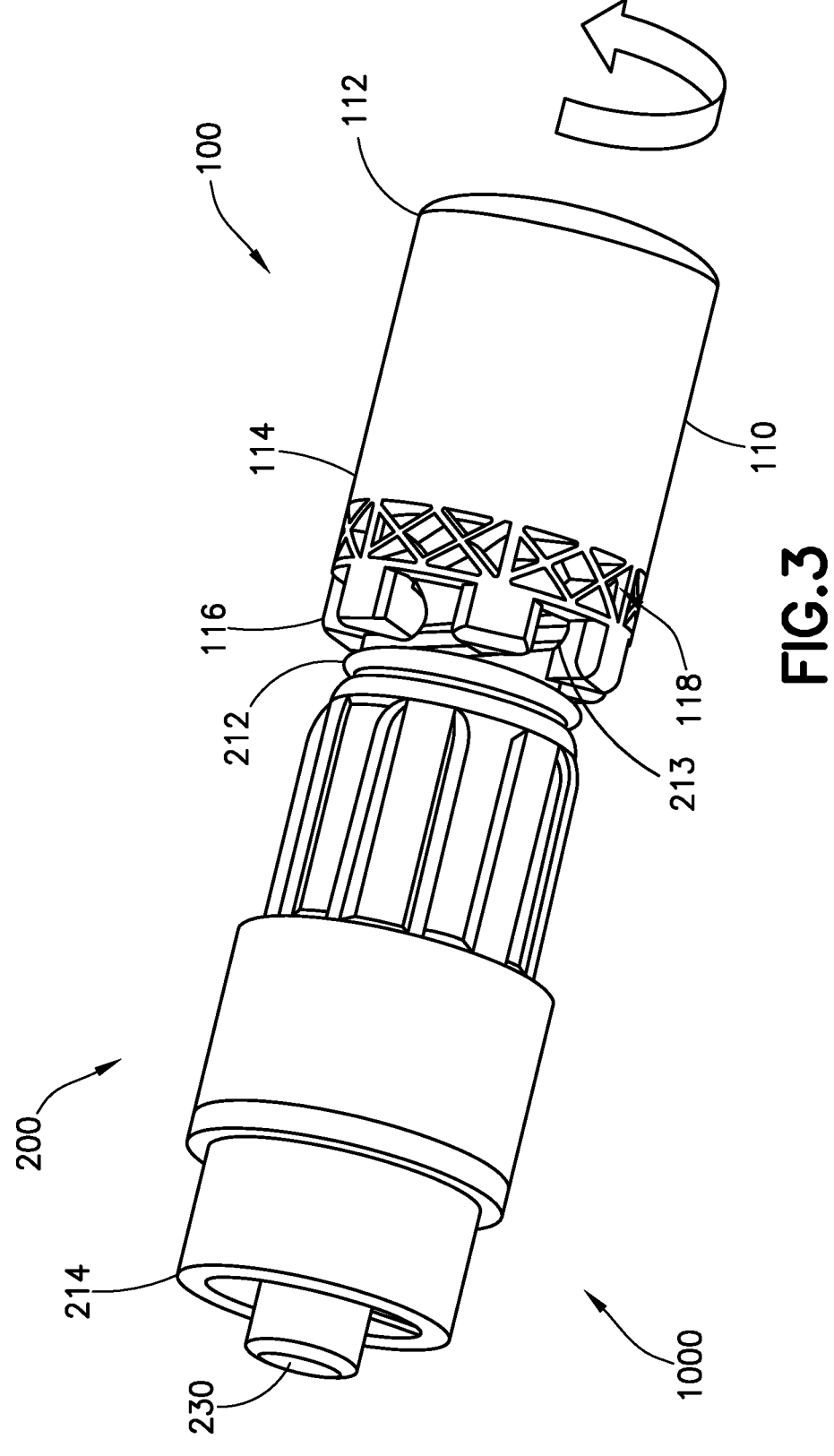
FIG. 3 is a perspective view of a system including a disinfection device according to non-limiting embodiments described herein.

Turning to FIG. 3, as shown, disinfection device 100 may be rotated to disinfect medical device 200. In non-limiting embodiments, based on presence of threads 213 on proximal end 212 of medical device 200, rotation of disinfection device 100 is, after a certain point, prevented by interaction of one or more flanges 116, threads 213, housing 210, and/or housing 110, resulting in mechanical forces being applied to deformable portion 118. In non-limiting embodiments described herein, for example where deformable portion 118 includes a mechanophoric material, such as a mechanochromic material, the application of mechanical forces causes a change in a property of deformable portion 118, for example a change in color, thus alerting a user to the presence of force, and optionally, an indication that the device has previously been used. In non-limiting embodiments in which deformable portion 118 is frangible, continued application of force may result in a breakage in housing 110 of disinfecting device 100.

Turning to FIGS. 4A and 4B, shown is a non-limiting embodiment of a disinfecting device 300 including a housing 310 having a proximal end 312, an open distal end 314, and a sidewall therebetween defining an interior 330. The interior 330 may be configured to receive a disinfection solution therein as described previously, optionally received and/or absorbed within a porous material 334 arranged within interior 330. Porous material 334 may be a sponge or other suitable material as described previously. In non-limiting embodiments, such as shown in FIG. 4B, interior 330 of housing 310 may include a projection 332, which may be arranged to provide mechanical support to at least a portion of porous material 334 received within interior 330, as described previously. As discussed briefly above, as shown in FIGS. 4A and 4B, flange 316 is a single flange that extends about the circumference of the housing 310, defining a central opening into which a medical device can be inserted, for example to snap-fit the medical device to housing 310. Housing 310 may, in some embodiments, include a label thereon, for example identifying the contents received therein. In non-limiting embodiments, a removable film, such as a peelable film, is arranged on distal end 314 of housing 310, providing liquid-tight and/or air-tight protection of distal end 314, porous material 334, and/or disinfection solution received within interior 330.

Disinfection device 300 may include a deformable portion 318. As discussed previously, deformable portion 318 may be a thinning of sidewall of housing 310, may be a web with one or more openings in sidewall of housing 310 (e.g., as shown in the attached figures), may include a different (e.g., weaker) material than the remainder of housing 310, and/or or any other known construction for providing one or more weaker points that are deformable. In non-limiting embodiments, deformable portion 318 is frangible, such that a distal end 314 of housing 310, for example including one or more flanges 316, is separable from the remainder of housing 310 upon the breaking of the deformable portion 318. In non-limiting embodiments, deformable portion 318 includes a mechanophoric material, such as a mechanochromic material, as described previously.

Figure 5A:
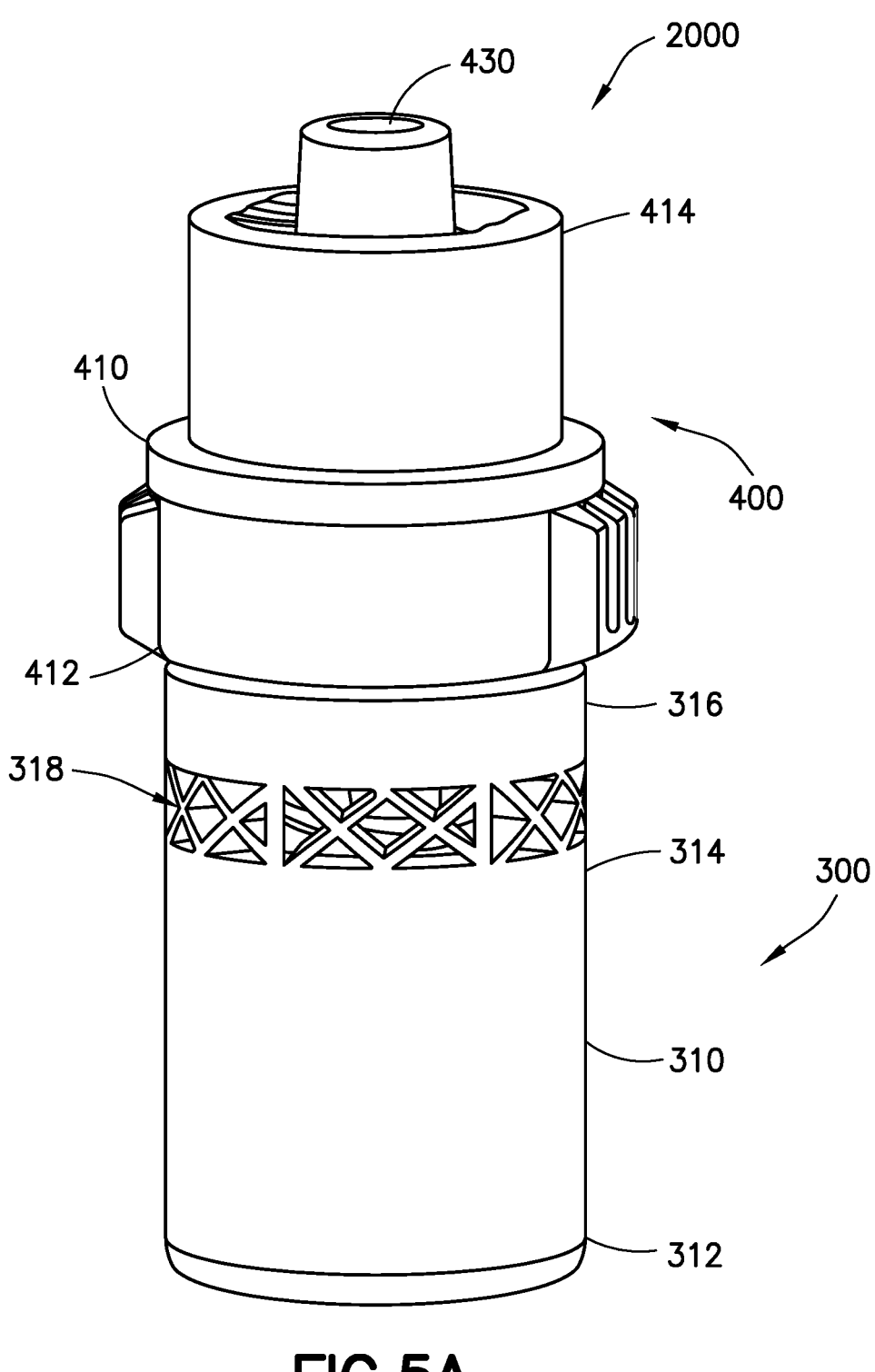
FIG. 5A is a side view of a system including a disinfection device according to non-limiting embodiments described herein.
Figure 5B:
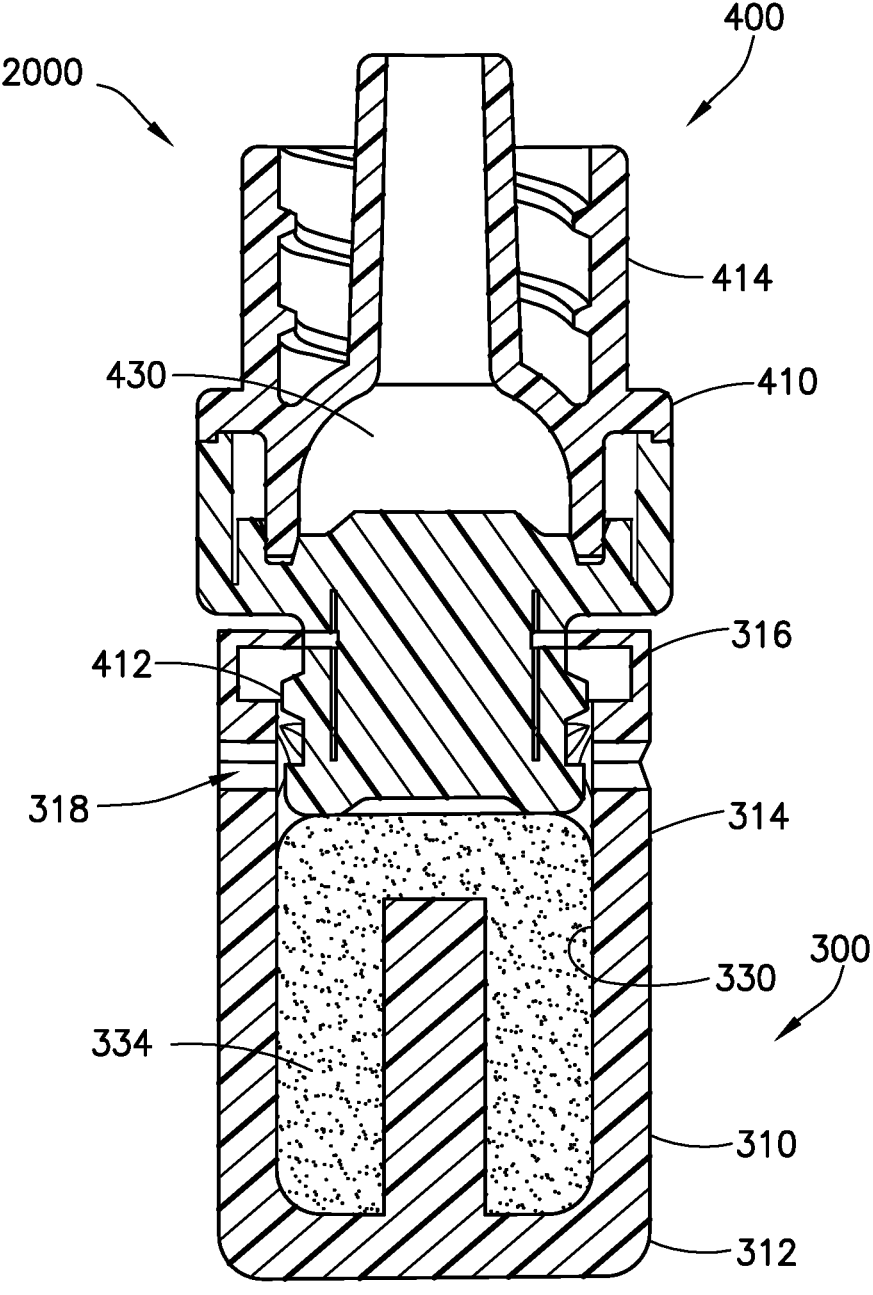
FIG. 5B is a cross-sectional view of a system including a disinfection device according to non-limiting embodiments described herein.
Figure 6:
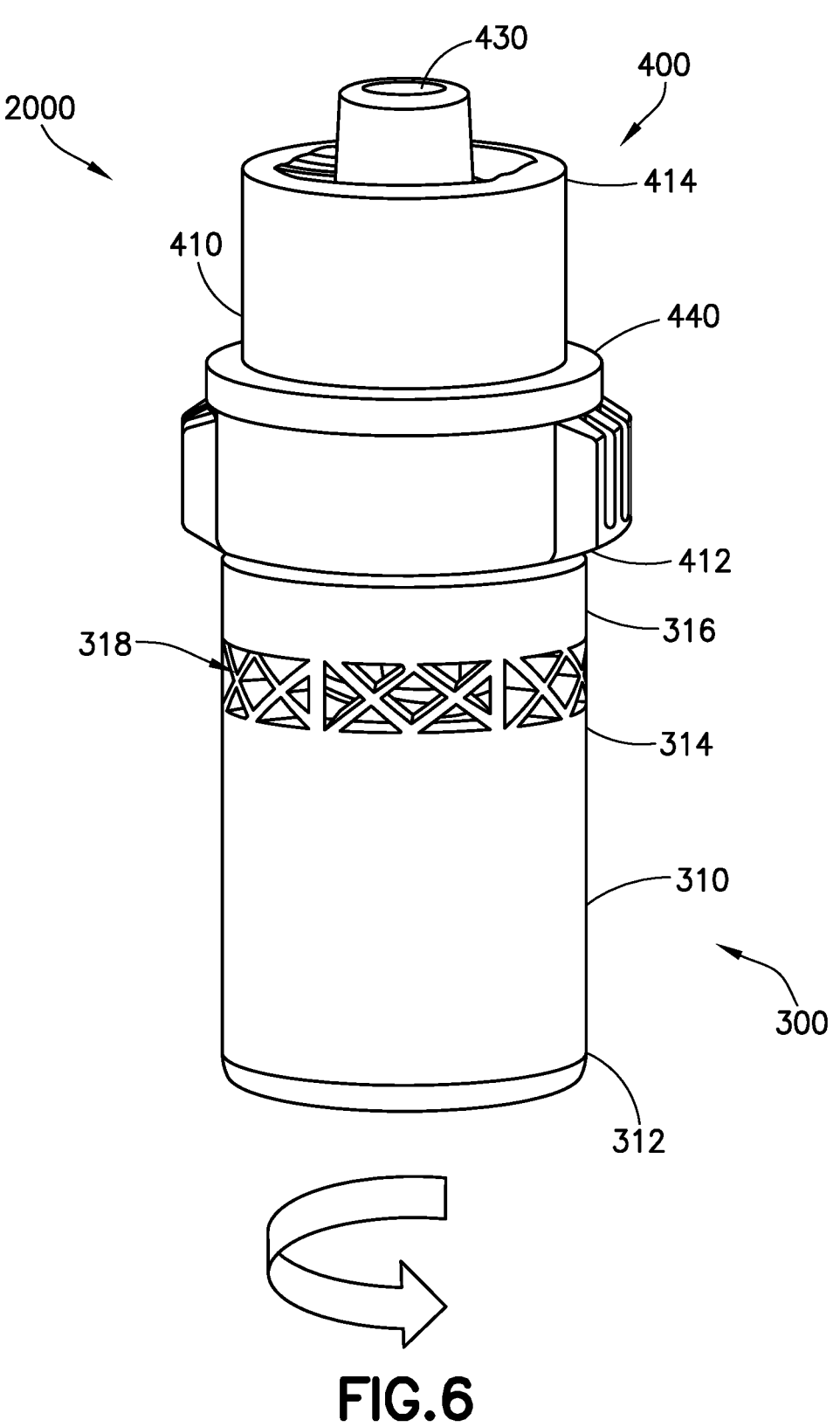
FIG. 6 is a side view of a system including a disinfection device according to non-limiting embodiments described herein.

Turning to FIGS. 5A-6, shown is a system 2000. Disinfecting device 300 may be as substantially described herein. Medical device 400, as described previously, may be any suitable medical device, and in the illustrated embodiments is a medical connector, such as an NFC. Medical device 400 may include a housing 410 having a proximal end 412 and a distal end 414 and a sidewall defining a fluid conduit 430. Proximal end 412 of device 400 may include any features for allowing connection of disinfecting device 300 or other medical devices, such as flange(s), thread(s), and/or the like. As shown in FIGS. 5A-5B, disinfection device 300 may be coupled to proximal end 412 of medical device 400 by one or more flanges 316. In this position, proximal end 412 of medical device 400 may be in contact with porous material 334 received within interior 330 of disinfection device 300. Disinfection device 330 may be rotatable relative to medical device 400, allowing for scrubbing of proximal end 412 of medical device 400 by porous material 334 and for disinfecting by a disinfection solution received within interior 330 of disinfecting device 300. As described previously, and as shown in FIG. 6, disinfection device 300 may be rotated to disinfect medical device 400. In non-limiting embodiments, based on presence of threads on proximal end 412 of medical device 400, rotation of disinfection device 300 is, after a certain point, prevented by interaction of one or more flanges 316, threads, housing 410, and/or housing 310, resulting in mechanical forces being applied to deformable portion 318. In non-limiting embodiments described herein, for example where deformable portion 318 includes a mechanophoric material, such as a mechanochromic material, the application of mechanical forces causes a change in a property of deformable portion 318, for example a change in color.

Also provided herein are kits, including a disinfecting device 100, 300 as substantially described herein, received within a packaging, such as a tearable packaging.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A disinfecting device, comprising:
a housing comprising a circumference, a closed proximal end, a distal end having an opening therein, and a sidewall therebetween defining an interior in fluid communication with the opening, the sidewall including a deformable portion and a remaining portion;
one or more flanges at the distal end of the housing comprising a radially inward-extending portion; and
a disinfecting solution absorbed within a porous material within the interior and adjacent the clos proximal end of the housing,
wherein the deformable portion extends about the circumference of the housing adjacent the one or more flanges at the distal end and between the one or more flanges and the porous material, the deformable portion integral with the housing, and the deformable portion weaker than a remaining portion of the sidewall and configured to provide to a user of the disinfecting device a visual indication that the disinfecting device has been used.

2. The disinfecting device of claim 1, further comprising a projection extending from the closed proximal end and configured to provide mechanical support to the porous material.

3. The disinfecting device of claim 2, wherein the projection is configured to improve contact between the porous material and a medical device to which the housing is coupled.

4. The disinfecting device of claim 3, wherein the one or more flanges are L-shaped, comprising the radially inward-extending portion.

5. The disinfecting device of claim 4, wherein the radially inward-extending portion is configured to snap-fit to a medical connector, optionally a needle-free connector (NFC).

6. The disinfecting device of claim 5, wherein the one or more flanges are configured such that the disinfecting device is rotatable relative to the medical connector.

7. The disinfecting device of claim 3, wherein the deformable portion comprises a web with one or more openings in the deformable portion of the sidewall.

8. The disinfecting device of claim 3, further comprising a removable film arranged over the distal end of the housing.

9. The disinfecting device of claim 3, wherein the disinfecting solution comprises chlorhexidine gluconate (CHG).

10. The disinfecting device of claim 3, wherein the disinfecting solution comprises isopropyl alcohol (IPA).

11. The disinfecting device of claim 3, wherein the disinfecting solution comprises from about 0.5% to about 4% CHG and about 70% IPA.

12. The disinfecting device of claim 7, wherein the deformable portion is frangible and is configured so that the one or more flanges are separable from the remainder of the housing upon breaking of the deformable portion.

13. The disinfecting device of claim 3, wherein the deformable portion comprises a mechanochromic material.

14. The disinfecting device of claim 13, wherein the deformable portion comprises a thinned portion of the sidewall that is weaker than the remainder of the sidewall.

15. The disinfecting device of claim 14, wherein the deformable portion is frangible and is configured so that the one or more flanges are separable from the remaining portion of the sidewall upon breaking of the deformable portion.

16. A system comprising:
a medical connector having a proximal end, a distal end, and a sidewall therebetween defining a fluid conduit; and
the disinfecting device of claim 3 coupled to the proximal end of the medical connector.

17. The system of claim 16, wherein the medical connector is a needle-free connector (NFC).

18. The system of claim 16, wherein the proximal end of the medical connector is threaded.

19. The system of claim 16, wherein the one or more flanges are configured to snap-fit to the medical connector.

20. The system of claim 19, wherein the one or more flanges are configured such that the disinfecting device is rotatable relative to the medical connector.

21. A kit comprising:
the disinfecting device according to claim 3; and
a packaging defining an interior in which the disinfecting device is received.

* * * * *